United States Patent
Dalko et al.

(10) Patent No.: US 10,995,051 B2
(45) Date of Patent: May 4, 2021

(54) METHOD FOR SYNTHESIZING NOVEL COMPOUNDS DERIVED FROM 3-HYDROXY-CYLOPENTYL ACETIC ACID

(71) Applicant: L'OREAL, Paris (FR)

(72) Inventors: Maria Dalko, Paris (FR); Xavier Marat, Aulnay-sous-Bois (FR); Julien Hitce, Aulnay-sous-Bois (FR); Chao-Jun Li, Quebec (CA)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/731,705

(22) Filed: Dec. 31, 2019

(65) Prior Publication Data

US 2020/0131108 A1    Apr. 30, 2020

Related U.S. Application Data

(62) Division of application No. 15/557,717, filed as application No. PCT/EP2016/055459 on Mar. 14, 2016, now Pat. No. 10,654,788.

(30) Foreign Application Priority Data

Mar. 13, 2015   (FR) ...................... 1500493

(51) Int. Cl.

| | | |
|---|---|---|
| C07C 45/69 | (2006.01) | |
| C07C 59/11 | (2006.01) | |
| C07C 51/38 | (2006.01) | |
| C07C 69/675 | (2006.01) | |
| C07C 45/54 | (2006.01) | |
| C07C 67/347 | (2006.01) | |
| C07C 69/757 | (2006.01) | |
| C07C 69/732 | (2006.01) | |
| C07C 69/734 | (2006.01) | |
| C07D 213/30 | (2006.01) | |
| A61K 8/365 | (2006.01) | |
| A61Q 17/00 | (2006.01) | |
| A61Q 19/00 | (2006.01) | |
| C07C 51/09 | (2006.01) | |
| C07C 59/54 | (2006.01) | |
| C07C 59/56 | (2006.01) | |
| C07C 59/72 | (2006.01) | |

(52) U.S. Cl.
CPC .............. *C07C 59/11* (2013.01); *A61K 8/365* (2013.01); *A61Q 17/00* (2013.01); *A61Q 19/00* (2013.01); *C07C 45/54* (2013.01); *C07C 45/69* (2013.01); *C07C 51/09* (2013.01); *C07C 51/38* (2013.01); *C07C 59/54* (2013.01); *C07C 59/56* (2013.01); *C07C 59/72* (2013.01); *C07C 67/347* (2013.01); *C07C 69/675* (2013.01); *C07C 69/732* (2013.01); *C07C 69/734* (2013.01); *C07C 69/757* (2013.01); *C07D 213/30* (2013.01); *C07C 2601/08* (2017.05); *C07C 2601/10* (2017.05); *C07C 2601/14* (2017.05)

(58) Field of Classification Search
CPC ..... C07C 45/69; C07C 47/222; C07C 49/597; C07C 45/61; C07C 51/38; C07C 62/02; C07D 213/30

See application file for complete search history.

(56) References Cited

U.S. PATENT DOCUMENTS

| | | |
|---|---|---|
| 4,603,146 A | 7/1986 | Kligman |
| 4,767,750 A | 8/1988 | Jacquet et al. |
| 2014/0050679 A1 | 2/2014 | Allemand et al. |

FOREIGN PATENT DOCUMENTS

| | | |
|---|---|---|
| DE | 102004009440 A1 | 9/2005 |
| EP | 0413528 A1 | 8/1990 |
| EP | 1333021 A2 | 8/2003 |
| EP | 1502909 A1 | 2/2005 |
| FR | 2375207 A1 | 7/1978 |
| FR | 2979232 A1 | 3/2013 |
| JP | S5432457 | 3/1979 |
| JP | S6226248 A | 2/1987 |
| JP | S6383049 A | 4/1988 |
| JP | 2005035939 | 2/2005 |
| JP | 2010111633 | 5/2010 |
| WO | 93/10756 A1 | 6/1993 |
| WO | 2012084699 A2 | 6/2012 |
| WO | 2012084701 A2 | 6/2012 |
| WO | 2013165478 A1 | 11/2013 |

OTHER PUBLICATIONS

Reischer et al. "Effects of natural and novel synthetic jasmonates in experimental metastatic melanoma" British Journa of Pharmacology, 2007, 150, pp. 738-749.

Kiyota et al. "Syntheses and odour descriptions of cyclopropanated compounds 2. Analogues of methyl jasmonate", Flavour and Fragrance Journal, 2002, p. 267-271, vol. 17.

Meyer et al. "Cucurbic Acid Related Metabolites of the PLant Growth Regulator Dihydrojasmonic Acid in Barley (*Hordeum volgare*)", Institute of Plant Biochemistry and Institute of Biology and Geology, University of Tromso, 1991, p. 401-408, vol. 187.

(Continued)

*Primary Examiner* — Deepak R Rao
(74) *Attorney, Agent, or Firm* — McNees Wallace & Nurick LLC

(57) ABSTRACT

The present invention relates to compounds of formula (I):

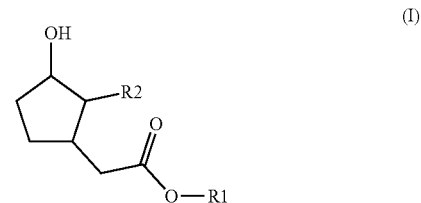

in which R1 is a hydrogen atom, a phenyl radical, or a straight or branched, saturated or unsaturated hydrocarbon radical having 1 to 8 carbon atoms.

12 Claims, No Drawings

(56) References Cited

OTHER PUBLICATIONS

D.C. Aldridge, et al., "Metabolites of Lasiodiplodia Theobromae," Journal of the Chemical Society, Perkin Transactions 1, Royal Society of Chemistry, Jan. 1, 1971, pp. 1623-1627.

P. Ducos, et al., "Coupures Thermiques Du Type Retro-Diels Et Alder-II," Tetrandron, vol. 29, No. 20, Jan. 1, 1973, pp. 3233-3236.

T. Kitahara, et al., Synthesis of Methyl Jasmonate and Methyl Cucurbate, Agricultural and Biological Chemistry, Agricultural Chemical Society of Japan, vol. 51, No. 4, Apr. 1, 1987, pp. 1129-1133.

Kang H. Park, II, et al., "A Pauson-Khand-Type Reaction Between Alkynes and Olefinic Aldehydes Catalyzed by Rhodium/Cobalt Heterobimetallic Nanoparticles: An Olefinic Aldehyde as an Olefin and Co Source," Organic Letters, vol. 6, No. 7, Apr. 1, 2004, pp. 1183-1186.

J. Takehara, et al., "Synthesis of Chiral Methyl Cucurbate and its Analogs," Agricultural and Biological Chemistry, vol. 55, No. 12, Jan. 1, 1991, pp. 2939-2944.

M. Sreekanth, et al., "Ti(III)-Mediated Opening of 2,3-Epoxy Alcohols to Build Five-Membered Carbocycles With Multiple Chiral Centres," Tetrahedron Letters, vol. 52, No. 14, Feb. 1, 2011, pp. 1709-1712.

Chen, Liang, et al. The first palladium-catalyzed 1,4-addition of terminal alkynes to conjugated enones, Chemical Communications, 2004, vol. 20, pp. 2362-2364.

Zhou, Feng, et al. Palladium-catalyzed 1,4-Addition of Terminal Alkynes to Conjugated Enones, Organic Syntheses, 2014, vol. 91, pp. 72-82.

Seto, Hideharu, et al. Structure-Activity Relationships of (+)-Cucurbic Acid Analogs on the Root Growth of Rice Seedlings and Height of Young Corn Plants, Journal of Pesticide Science, 1992, vol. 17, pp. 61-67.

Tanaka, Ken, et al. Rhodium-Catalyzed Regio-, Diastereo-, and Enantioselective Intermolecular [4+2] Carbocyclization of 4-Alkynals with Electron-Deficient Alkenes, European Journal of Organic Chemistry, 2006, vol. 16, pp. 3582-3595.

STN RN 1560355-62-5, (2014).

Mase et al., "Organocatalytic Enantioselective Michael Additions of Malonates to 2-Cyclopentenone," Synlett, vol. 2010, No. 15, pp. 2340-2344 (Sep. 2010).

METHOD FOR SYNTHESIZING NOVEL COMPOUNDS DERIVED FROM 3-HYDROXY-CYLOPENTYL ACETIC ACID

The present invention relates to a process for preparing compounds derived from 3-hydroxycylopentyl acetic acid and also to compounds derived from 3-hydroxycylopentyl acetic acid and to the use of compounds derived from 3-hydroxycylopentyl acetic acid for promoting skin desquamation and/or stimulating epidermal renewal and/or combating skin aging. The invention also relates to compositions, in particular cosmetic compositions, which can be used for promoting skin desquamation and/or stimulating epidermal renewal and/or combating intrinsic and/or extrinsic skin aging.

Desquamation is a natural phenomenon associated with the fact that the epidermis, which constitutes the upper layer of the skin, is constantly being regenerated. The epidermis is constituted of several layers of cells, the deepest of which is the basal layer constituted of undifferentiated cells. Over time, these cells will differentiate and migrate to the surface of the epidermis while constituting the various layers thereof, until they form, at the surface of the epidermis, the corneocytes which are dead cells that are eliminated by desquamation. This loss at the surface is compensated for by the migration of cells from the basal layer toward the surface of the epidermis. There is perpetual renewal of the skin. A forced removal of the horny layer accelerates the renewal and makes it possible to combat aging.

At the same time, these cells continue their differentiation, the final stage of which is the corneocyte. These are in fact dead cells which constitute the final layer of the epidermis, that is to say the outermost layer, also called stratum corneum.

Skin aging resulting from intrinsic or extrinsic factors results in the appearance of wrinkles and fine lines, in yellowing of the skin which develops a weathered look accompanied by the appearance of pigment spots, in disorganization of the elastin and collagen fibers leading to a loss of elasticity, of suppleness and firmness, or in the appearance of telangiectasia.

Some of these signs of aging are more particularly associated with intrinsic or physiological aging, that is to say "normal" aging associated with age or chronobiological aging, whereas others are more specific for extrinsic aging, that is to say aging generally caused by the environment; this is more particularly photoaging due to exposure to the sun, to light or to any other radiation.

The invention focuses on intrinsic or physiological aging and also on extrinsic aging.

The skin changes due to intrinsic aging are the consequence of genetically programmed senescence in which endogenous factors are involved. This intrinsic aging causes in particular a slowing of skin cell renewal, which is essentially reflected by the occurrence of detrimental clinical modifications, such as a reduction in subcutaneous adipose tissue and the appearance of fine wrinkles or fine lines, and by histopathological changes, such as an increase in the number and thickness of elastic fibers, a loss of vertical fibers of the elastic tissue membrane, and the presence of large irregular fibroblasts in the cells of this elastic tissue.

Conversely, extrinsic aging leads to clinical modifications such as thick wrinkles and the formation of a flaccid, tanned skin, and histopathological changes such as an excessive accumulation of elastic matter in the upper dermis and collagen fiber degeneration.

Various agents intended for combating skin aging are known in the art.

Thus, U.S. Pat. No. 4,603,146 describes the use of retinoic acid and derivatives thereof in cosmetic compositions, for the purpose of combating skin aging.

Moreover, many patents and publications (see for example application EP-A-413528) and also many commercial cosmetic compositions teach the use of α-hydroxy acids, such as lactic acid, glycolic acid or else citric acid, for treating skin aging.

Finally, β-hydroxy acids and more especially salicylic acid and also derivatives thereof are known for their desquamating properties (see documents WO-A-93/10756 and U.S. Pat. No. 4,767,750).

All these compounds have an action against skin aging by promoting desquamation, that is to say the removal of dead cells located at the surface of the horny layer of the epidermis. This "desquamating" property is also called, often wrongly, keratolytic property.

However, these prior art compounds also have side-effects, which consist of tingling, tautness, hotness and redness that are unpleasant for the user.

Also known from application EP 1 333 021 are cosmetic or pharmaceutical compositions comprising jasmonic acid derivatives and also the use of these derivatives for promoting skin desquamation and/or stimulating epidermal renewal and/or combating skin aging.

The process according to the present invention enables the synthesis of novel compounds derived from 3-hydroxycylopentyl acetic acid; it enables the synthesis of a family of compounds which exhibit great structural diversity that cannot be obtained by means of the reagents used in the prior art processes, in particular by using the methyl jasmonate used in the syntheses of application EP 1 333 021.

In addition, the process according to the present invention is an environmentally friendly process which adheres to the principles of green chemistry, among which mention may be made of a limited number of steps, the use of as few atoms as possible, the use of renewable solvents which have a limited impact on the environment, and minimization of waste, more particularly in the case where steps a) and b) are carried out in the same reactor.

In addition, the compounds synthesized by means of the process according to the invention have satisfactory properties in terms of promoting skin desquamation and/or stimulating epidermal renewal.

In addition, the compounds according to the present invention that are used as anti-aging agents have an action that is at least as efficient as that of the prior art compounds, but without having their drawbacks.

Thus, a purpose of the invention is to provide a novel process for synthesizing compounds derived from 3-hydroxycylopentyl acetic acid from acrolein, from an alkyne and from a malonate derivative. This synthesis process makes it possible to obtain a wide family of compounds, among which some have never been described.

A purpose of the invention is also to overcome the drawbacks of the prior art compounds and to provide novel compounds capable of promoting skin desquamation and/or stimulating epidermal renewal, the use of which does lead to tingling, tautness, hotness or redness that are unpleasant for the user.

Thus, according to a first aspect, the present invention relates to a process for preparing a compound of formula (I):

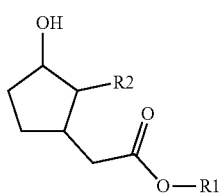

wherein R1 represents a hydrogen atom, a phenyl radical or a linear or branched, saturated or unsaturated hydrocarbon-based radical containing 1 to 8 carbon atoms, R2 denotes a radical chosen from:
- a linear, branched or cyclic, saturated hydrocarbon-based radical containing 1 to 12 carbon atoms, optionally substituted with 1 to 3 groups, which may be identical or different, chosen from —OR31, —NR31R41, —COOR31, —OCOR31 and halogens, with R31 and R41 representing, independently of one another, a hydrogen atom, a phenyl radical or a linear or branched, saturated or unsaturated alkyl radical containing 1 to 4 carbon atoms;
- a radical —Ar—R22 with Ar being an aromatic nucleus chosen from phenyl or pyridyl groups, and R22 representing a substituent of the aromatic nucleus Ar, chosen from hydrogen, —OR', —NO$_2$, halogens, —NH$_2$, —CF$_3$ and —R', with R' denoting a hydrogen atom, a linear, branched or cyclic, saturated or unsaturated hydrocarbon-based radical containing 1 to 6 carbon atoms, or a phenyl radical;
- a radical —R23-Ph wherein R23 represents a linear or branched, saturated or unsaturated hydrocarbon-based divalent radical containing 1 to 6 carbon atoms, optionally substituted with 1 to 3 —OH groups and/or optionally interrupted with 1 to 3 non-adjacent oxygen atoms, Ph representing a phenyl group;
- a radical —R24-NH—R34 with R24 representing a linear or branched, saturated or unsaturated hydrocarbon-based divalent radical containing 1 to 4 carbon atoms, optionally substituted with 1 to 3 —OH groups and/or optionally interrupted with 1 to 3 oxygen atoms; R34 representing a substituent —COOR' or a linear or branched, saturated or unsaturated hydrocarbon-based radical containing 1 to 4 carbon atoms, optionally interrupted with an NH, O or S group, with R' representing a hydrogen atom, a linear, branched or cyclic, saturated hydrocarbon-based radical containing 1 to 6 carbon atoms, such as a tert-butyl radical, or a phenyl radical;
- a radical —CO—O—R25 wherein R25 represents a hydrogen atom, a phenyl radical or a linear or branched, saturated or unsaturated hydrocarbon-based radical containing 1 to 8 carbon atoms;

and also the optical isomers, diastereoisomers and/or corresponding salts thereof;

in which process the following steps are carried out:
a) 1,4 addition to acrolein of an alkyne of formula R2C≡H with R2 as defined in formula (I) above;
b) cyclization of the product obtained at the end of step a) by intramolecular hydroacylation;
c) 1,4 addition to the cyclopentenone resulting from step b) of the malonate derivative CH$_2$(CO$_2$CH$_2$Ph)(CO$_2$R0) for which, when in formula (I) R1 is a hydrogen atom, then —R0 is —CH$_2$Ph and when in formula (I) R1 is not a hydrogen atom, then R0 is R1;
d) reduction and decarboxylation of the product obtained in step c).

According to a second aspect, the present invention relates to the use, for promoting skin desquamation and/or stimulating epidermal renewal and/or combating skin aging, of a compound of formula (I) wherein R1 and R2 are as defined above with the exclusion of the compounds of formula (I) for which R2 is a pentyl radical and R1 is a hydrogen atom or a methyl group.

According to yet another of its aspects, the present invention relates to compounds of formula (I):

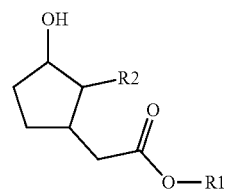

wherein R1 represents a hydrogen atom, a phenyl radical or a linear or branched, saturated or unsaturated hydrocarbon-based radical containing 1 to 8 carbon atoms, R2 denotes a radical chosen from:
- a linear, branched or cyclic, saturated hydrocarbon-based radical containing 1 to 12 carbon atoms, optionally substituted with 1 to 3 groups, which may be identical or different, chosen from —OR31, —NR31R41, —COOR31, —OCOR31 and halogens, with R31 and R41 representing, independently of one another, a hydrogen atom, a phenyl radical or a linear or branched, saturated or unsaturated alkyl radical containing 1 to 4 carbon atoms with the exclusion of the compounds of formula (I) for which R2 is a pentyl radical and R1 is a hydrogen atom or a methyl group;
- a radical —Ar—R22 with Ar being an aromatic nucleus chosen from phenyl or pyridyl groups, and R22 representing a substituent chosen from hydrogen, —OR', —NO$_2$, halogens, —NH$_2$, —CF$_3$ and —R', with R' denoting a hydrogen atom, a linear, branched or cyclic, saturated or unsaturated hydrocarbon-based radical containing 1 to 6 carbon atoms, or a phenyl radical;
- a radical —R23-Ph wherein R23 represents a linear or branched, saturated or unsaturated hydrocarbon-based divalent radical containing 1 to 6 carbon atoms, optionally substituted with 1 to 3 —OH groups and/or optionally interrupted with 1 to 3 non-adjacent oxygen atoms, Ph representing a phenyl group; with the exclusion of the compounds

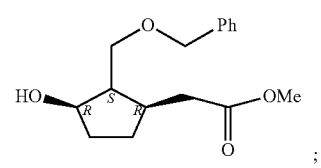

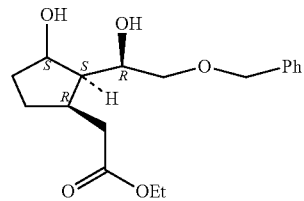

a radical —R24-NH—R34 with R24 representing a linear or branched, saturated or unsaturated hydrocarbon-based divalent radical containing 1 to 4 carbon atoms, optionally substituted with 1 to 3 —OH groups and/or optionally interrupted with 1 to 3 oxygen atoms; R34 representing a substituent —COOR' or a linear or branched, saturated or unsaturated hydrocarbon-based radical containing 1 to 4 carbon atoms, optionally interrupted with an NH, O or S group, with R' representing a hydrogen atom, a linear, branched or cyclic, saturated hydrocarbon-based radical containing 1 to 6 carbon atoms, or a phenyl radical;

a radical —CO—O—R25 wherein R25 represents a hydrogen atom, a phenyl radical or a linear or branched, saturated or unsaturated hydrocarbon-based radical containing 1 to 8 carbon atoms with the exclusion of the compound

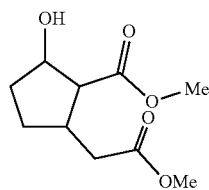

and also the optical isomers, diastereoisomers and/or corresponding salts thereof.

The salts that may be used according to the invention are chosen in particular from salts of alkali metal or alkaline-earth metal, such as sodium, potassium or calcium, or else from zinc, magnesium or strontium salts, salts of an organic amine, such as natural amino acids, in particular lysine and arginine, or quaternary ammonium salts.

The present invention also relates to a composition, in particular a cosmetic composition, comprising a compound of formula (I) according to the present invention.

The invention will be understood more clearly on reading the detailed description and the examples that follow.

DETAILED DESCRIPTION

The term "hydrocarbon-based radical containing 1 to 12 carbon atoms" is intended to mean a hydrocarbon-based radical containing 1, 2, 3, 4, 5, 6, 7, 8, 9, 10, 11 or 12 carbon atoms.

The term "halogen atom" is intended to mean an atom chosen from F, Cl, Br and I.

The present invention relates to a novel process for synthesizing compounds derived from 3-hydroxycyclopentyl acetic acid from acrolein, from an alkyne and from a malonate derivative, in which process the following steps are carried out:
a) 1,4 addition to acrolein of an alkyne of formula R2C≡H with R2 as defined in formula (I) above;
b) cyclization of the product obtained at the end of step a) by intramolecular hydroacylation;
c) 1,4 addition to the cyclopentenone resulting from step b) of the malonate derivative $CH_2(CO_2CH_2Ph)(CO_2R0)$ for which, when in formula (I) R1 is a hydrogen atom, then —R0 is —$CH_2Ph$ and when in formula (I) R1 is not a hydrogen atom, then R0 is R1;
d) reduction and decarboxylation of the product obtained in step c).

The process according to the invention is particularly environmentally friendly, it adheres to the principles of green chemistry: a limited number of steps, the use of as few atoms as possible in order to minimize the resources consumed, use of some reagents in catalytic rather than stoichiometric amounts, the use of renewable solvents which have a limited impact on the environment, and minimization of waste, in particular in the case where steps a) and b) are linked together in the same reactor.

In addition, the starting substrates, in particular acrolein, are readily accessible.

This process is characterized in that the overall synthesis route is very direct and that it uses acrolein as starting product for the 1,4 addition of an alkyne, and yet acrolein is a substrate that is "difficult" to use since it is not very stable and is very reactive: it tends to polymerize.

Moreover, the operating conditions and in particular the $Pd(OAc)_2/PMe_3$ catalytic system indeed make it possible to promote the 1,4 addition relative to decomposition of the acrolein.

This process is summarized in scheme 1 below:

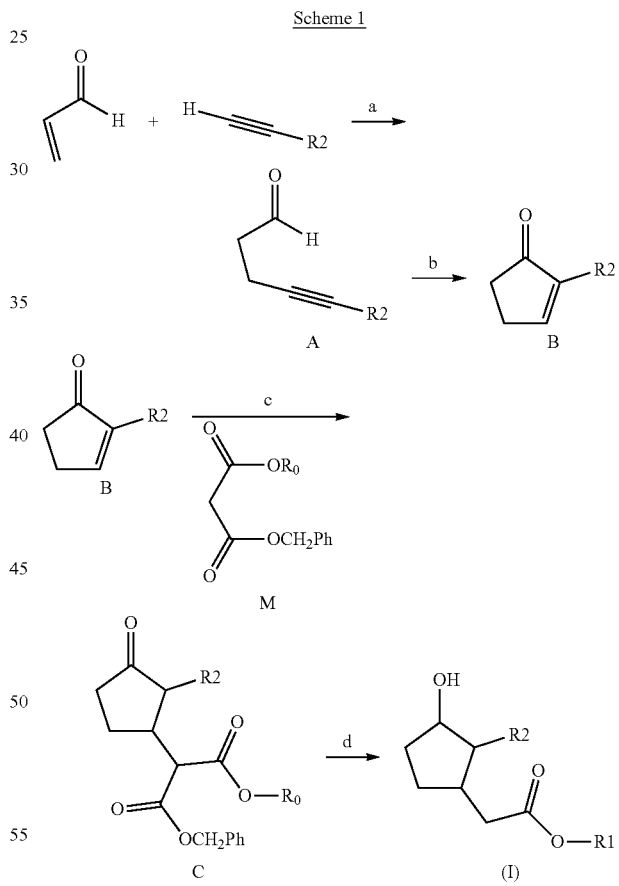

Step a)

In step a) a 1,4 addition of the true alkyne of formula R2C≡H to acrolein is carried out. The alkyne and the acrolein are heated to a temperature between 30° C. and 140° C., preferably between 100 and 120° C., in water or in an organic solvent or in a mixture of at least two miscible or immiscible solvents, in the presence of a catalyst. Preferably, the solvent is water, acetone, a toluene/water mixture or a toluene/acetone mixture.

More particularly, the acrolein and the alkyne R2C≡H are heated at 30-140° C. in the presence of a transition metal referred to as Mt-a, introduced in a catalytic amount ranging from 0.001 equivalent (equiv.) to 0.5 equiv., for a period ranging from 5 min to 24 h in an organic solvent which is preferably a mixture of at least 2 miscible or immiscible solvents chosen from toluene, benzene, water, methanol, ethanol, isopropanol, acetone, methyl ethyl ketone, THF, Me-THF, diethyl ether, diisopropyl ether, dichloromethane and acetonitrile.

Preferably, step a) is carried out in the presence of a catalyst which is a palladium complex in particular chosen from $Pd(OAc)_2$, $Pd(TFA)_2$, $Pd(OPiv)_2$, $PdCl_2$ and $Pd_2dba_3$ optionally combined with a phosphine or a rhodium complex optionally combined with a phosphine.

The transition metal Mt-a may also be a complex of rhodium combined with a phosphine.

Advantageously, the palladium complex is combined with a phosphine, such as $PMe_3$, $PPh_3$, $P(n-Bu)_3$ or $PCy_3$.

Particularly preferably, the transition metal introduced in a catalytic amount is a complex of palladium combined with trimethylphosphine. Preferably, the catalyst is $Pd(OAc)_2$ and the phosphine is $PMe_3$. They are advantageously used in a $Pd(OAc)_2/PMe_3$ mole ratio of 1/3.

According to one variant, the catalyst is preferably formed by heating, at a temperature ranging from 40 to 140° C., $Pd(OAc)_2$ in an amount ranging from 0.001 to 0.1 equiv. and $PMe_3$ in an amount ranging from 0.001 to 0.3 equiv. in toluene for a period ranging from 2 to 60 min.

According to one variant, the reaction is carried out in a mixture of 2 solvents chosen from toluene, benzene, water, methanol, acetone, methyl ethyl ketone, THF, Me-THF, diethyl ether, diisopropyl ether, dichloromethane and acetonitrile, advantageously in a mixture of toluene and of a more polar solvent such as water, methanol, acetone or acetonitrile.

Particularly preferably, the reaction is carried out in a mixture of toluene and water or a mixture of toluene and acetone.

At the end of the reaction, the reaction mixture is diluted in an organic solvent such as diethyl ether, diisopropyl ether, ethyl acetate or isopropyl acetate, and the phases are separated. The aqueous phase is extracted, for example 3 times with the same organic solvent, and the organic phases are combined, dried over $MgSO_4$ and concentrated under reduced pressure.

At the end of the reaction, the product obtained can optionally be isolated, before proceeding to step b.

In one preferred variant of the invention, step a and step b are carried out in the same reactor without isolating the intermediate resulting from step a. According to this variant, even more preferably, step a and step b are carried out in the same solvent system.

Alternatively, if it is desired to isolate the product from the reaction of step a) (intermediate A), the residue can be purified according to a conventional method such as silica gel column chromatography.

Step b)

In step b), an intramolecular hydroacylation is carried out, resulting in the cyclization of the product resulting from step a). At the end of step b), a cyclopentenone is obtained.

The intermediate A, which is the product resulting from step a), is heated to a temperature between 40° C. and 140° C. in an organic solvent in the presence of a catalyst.

The adduct resulting from step a is heated to 40-140° C. in the presence of a transition metal, referred to as Mt-b, which is identical to or different than that used in step a, and introduced in a catalytic amount, preferably ranging from 0.001 equiv. to 0.5 equiv., preferably for a period ranging from 5 min to 24 h in at least one solvent. Advantageously, the solvent is chosen from toluene, benzene, water, methanol, ethanol, isopropanol, acetone, methyl ethyl ketone, THF, Me-THF, diethyl ether, diisopropyl ether, dichloromethane and acetonitrile.

Preferably, the transition metal [Mt-b] introduced in a catalytic amount is a complex of palladium combined with a phosphine, a complex of rhodium combined with a phosphine, a complex of ruthenium combined with a phosphine or a complex of iridium combined with a phosphine.

Particularly preferably, the transition metal introduced in a catalytic amount is a complex of rhodium combined with a phosphine chosen from bidentate phosphines, such as ethylenebis(diphenylphosphine) (dppe), 1,4-bis(diphenylphosphino)propane (dppp), 1,4-bis(diphenylphosphino) butane (dppb), 1,4-bis(diphenylphosphino)ferrocene (dppf), 1,1'-binaphthalene-2,2'-diyl)bis(diphenylphosphine) (BINAP) and 2,2'-bis(di-p-tolylphosphino)-1,1'-binaphthyl (tol-BINAP). The conditions for this rhodium-catalyzed intramolecular hydroacylation reaction are in particular described in Tanaka and Fu (*J. Am. Chem. Soc.* 2001, 123, 11492).

According to one particular implementation, the rhodium complex $[Rh(dppe)]_2(BF_4)_2$ (0.001 equiv. to 0.5 equiv.) and the intermediate A (1 equiv.) are dissolved in a solvent such as water, toluene, dichloromethane, THF, Me-THF, diethyl ether, diisopropyl ether, methanol, ethanol, acetone, methyl ethyl ketone or acetonitrile, under an inert atmosphere. The reaction mixture is stirred for a period ranging from 5 min to 72 h at a temperature of between 18 and 150° C. After a return to ambient temperature, acetonitrile is added and the solvents are evaporated off under reduced pressure. The residue is purified according to a conventional method such as distillation and silica gel column chromatography. The cyclopentenone of formula B is thus obtained.

Step c)

In step c), a 1,4 addition of the malonate derivative M to the cyclopentenone of formula B resulting from step b) is carried out. The malonate derivative is treated with a strong base in an organic solvent, and is then brought into contact with the cyclopentenone.

More particularly, the malonate derivative M is treated with a strong base for a period ranging from 5 min to 24 h in at least one organic solvent, preferably chosen from N,N-dimethylformamide, N,N-dimethylacetamide, methanol, ethanol, isopropanol, tert-butanol, THF, Me-THF, diethyl ether, diisopropyl ether or dichloromethane, and then brought into contact with the cyclopentenone resulting from step b).

Preferably, the strong base is magnesium diethanolate, potassium tert-butanolate, sodium methoxide or lithium diisopropylamide.

Preferably, the solvent is methanol, N,N-dimethylformamide, tert-butanol or THF.

According to one preferred implementation of the invention, 1 equivalent of malonate $CH_2(CO_2CH_2Ph)(CO_2R0)$ is dissolved in an organic solvent which is preferably N,N-dimethylformamide, N,N-dimethylacetamide, THF or diethyl ether.

The malonate M, in an amount ranging from 1 to 10 equivalents, is then treated, at a temperature between −78° C. and 30° C., with an amount ranging from 1 to 5 equivalents of a strong base, which is preferably chosen from magnesium diethanolate, potassium tert-butanolate, sodium methoxide or lithium diisopropylamide.

The reaction medium is stirred for a period ranging from 5 to 120 min, then 1 equivalent of the cyclopentenone B, dissolved beforehand in the reaction solvent, is added dropwise.

The reaction mixture is stirred for a period ranging from 5 minutes to 24 h and then cooled to a temperature of between −30 and 0° C. The excess base is neutralized by adding a saturated aqueous $NH_4Cl$ solution and the adduct C is extracted from 1 to 4 times, using an organic solvent such as diethyl ether, diisopropyl ether, ethyl acetate or isopropyl acetate. The organic phases are combined, dried over $Na_2SO_4$ and concentrated under reduced pressure. The residue is purified by conventional methods such as silica gel column chromatography, in order to isolate the intermediate C.

Step d

In step d), a reduction and a decarboxylation of the intermediate C are carried out concomitantly. The intermediate C is brought into contact with a hydride donor in the presence of a hydrogenation catalyst in at least one organic solvent. The reaction mixture is then heated to a temperature of between 50 and 200° C. and preferably between 100 and 200° C.

The adduct C resulting from step c) is brought into contact with a hydride donor in the presence of a hydrogenation catalyst, referred to as Mt-d, introduced in a catalytic amount ranging from 0.001 equiv. to 0.5 equiv., for a period ranging from 5 min to 24 h in at least one solvent which is preferably chosen from toluene, benzene, water, methanol, ethanol, isopropanol, acetone, methyl ethyl ketone, THF, Me-THF, diethyl ether, diisopropyl ether, dichloromethane and acetonitrile. The reaction mixture is then heated at a temperature of between 50 and 200° C. and over a period ranging from 5 min to 24 hours in an autoclave.

Preferably, the hydride donor is dihydrogen or cyclohexane, and the solvent is chosen from water, methanol, ethanol, isopropanol, acetone, methyl ethyl ketone, THF, Me-THF, diethyl ether, diisopropyl ether and dichloromethane.

Preferably, the hydrogenation catalyst is based on at least one metal chosen from palladium, ruthenium, iridium and rhodium. Particularly preferably, the hydrogenation catalyst is palladium-on-carbon.

According to one preferred implementation of the invention, the intermediate C, dissolved beforehand in an organic solvent such as methanol, ethanol, isopropyl, THF, Me-THF, diethyl ether, diisopropyl ether or dichloromethane, is stirred at a temperature of between 18 and 100° C., under an atmosphere of dihydrogen in the presence of a hydrogenation catalyst such as palladium-on-carbon, for a period ranging from 5 min to 24 h. The hydrogen is then removed by passing a stream of argon and the mixture is heated to a temperature between 50 and 180° C. After a return to ambient temperature, the hydrogenation catalyst is filtered off on celite. The filtrate is concentrated under reduced pressure and the residue is purified by silica gel column chromatography in order to isolate the compound (I).

The process according to the present invention makes it possible, in particular, to obtain the compounds described hereinafter in a general manner, and also to obtain the preferred families of novel compounds according to the present invention and the novel individual compounds described hereinafter, and also the optical isomers, diastereoisomers and corresponding salts thereof.

The process according to the present invention advantageously makes it possible to obtain the compounds of formula (I) for which R1 is hydrogen or an ethyl group, R2 being as defined above.

The process according to the present invention makes it possible in particular to obtain the compounds of formula (I) for which R1 represents a hydrogen atom or a linear or branched, saturated hydrocarbon-based radical containing 1 to 4 carbon atoms, such as an ethyl radical, and R2 is a linear, branched or cyclic, saturated hydrocarbon-based radical containing 1 to 12 carbon atoms, optionally substituted with 1 or 2 groups, which may be identical or different, chosen from —OR31, NR31R41, COOR31 and halogen with R31 and R41 representing, independently of one another, a hydrogen atom or a linear or branched, saturated hydrocarbon-based radical containing 1 to 4 carbon atoms, and also the salts, isomers and solvates thereof.

The process according to the present invention makes it possible in particular to obtain the following compounds presented in table 1 below.

TABLE 1

| No. | Structure R1 = H | No. | Structure R1 = $C_2H_5$ |
|---|---|---|---|
| 1 | | 1' | |
| 2 | | 2' | |

TABLE 1-continued

| No. | Structure R1 = H | No. | Structure R1 = C$_2$H$_5$ |
|---|---|---|---|
| 3 | | 3' | |
| 4 | | 4' | |
| 5 | | 5' | |
| 6 | | 6' | |
| 7 | | 7' | |
| 8 | | 8' | |

TABLE 1-continued

| No. | Structure R1 = H | No. | Structure R1 = C₂H₅ |
|---|---|---|---|
| 9 | | 9' | |
| 10 | | 10' | |
| 11 | | 11' | |
| 12 | | 12' | |
| 13 | | 13' | |
| 14 | | 14' | |
| 15 | | 15' | |

TABLE 1-continued

| No. | Structure R1 = H | No. | Structure R1 = C$_2$H$_5$ |
|---|---|---|---|
| 16 | (structure: cyclopentane with OH, 4-ethynylphenyl, CH$_2$C(O)OR$_1$) | 16' | (structure: cyclopentane with OH, 4-ethynylphenyl, CH$_2$C(O)OR$_1$) |
| 17 | (structure: cyclopentane with OH, 4-bromophenyl, CH$_2$C(O)OR$_1$) | 17' | (structure: cyclopentane with OH, 4-bromophenyl, CH$_2$C(O)OR$_1$) |
| 18 | (structure: cyclopentane with OH, 4-fluorophenyl, CH$_2$C(O)OR$_1$) | 18' | (structure: cyclopentane with OH, 4-fluorophenyl, CH$_2$C(O)OR$_1$) |
| 19 | (structure: cyclopentane with OH, 4-hydroxyphenyl, CH$_2$C(O)OR$_1$) | 19' | (structure: cyclopentane with OH, 4-hydroxyphenyl, CH$_2$C(O)OR$_1$) |
| 20 | (structure: cyclopentane with OH, 4-phenylphenyl, CH$_2$C(O)OR$_1$) | 20' | (structure: cyclopentane with OH, 4-phenylphenyl, CH$_2$C(O)OR$_1$) |
| 21 | (structure: cyclopentane with OH, 4-trifluoromethylphenyl, CH$_2$C(O)OR$_1$) | 21' | (structure: cyclopentane with OH, 4-trifluoromethylphenyl, CH$_2$C(O)OR$_1$) |
| 22 | (structure: cyclopentane with OH, 3-hydroxyphenyl, CH$_2$C(O)OR$_1$) | 22' | (structure: cyclopentane with OH, 3-hydroxyphenyl, CH$_2$C(O)OR$_1$) |

TABLE 1-continued

| No. | Structure R1 = H | No. | Structure R1 = C₂H₅ |
|---|---|---|---|
| 23 | | 23' | |
| 24 | | 24' | |
| 25 | | 25' | |
| 26 | | 26' | |
| 27 | | 27' | |
| 28 | | 28' | |
| 29 | | 29' | |

TABLE 1-continued

| No. | Structure R1 = H | No. | Structure R1 = C$_2$H$_5$ |
|---|---|---|---|
| 30 | | 30' | |
| 31 | | 31' | |
| 32 | | 32' | |
| 33 | | 33' | |
| 34 | | 34' | |
| 35 | | 35' | |

TABLE 1-continued

| No. | Structure R1 = H | No. | Structure R1 = C₂H₅ |
|---|---|---|---|
| 36 | | 36' | |
| 37 | | 37' | |
| 38 | | 38' | |
| 39 | | 39' | |
| 40 | | 40' | |
| 41 | | 41' | |
| 42 | | 42' | |

TABLE 1-continued

| No. | Structure R1 = H | No. | Structure R1 = C₂H₅ |
|---|---|---|---|
| 43 | (cyclopentane with OH, CH₂CH₂CH₂Cl substituent, and CH₂C(O)OR₁ group) | 43' | (cyclopentane with OH, CH₂CH₂CH₂Cl substituent, and CH₂C(O)OR₁ group) |
| 44 | (cyclopentane with OH, C(CH₃)₂OH substituent, and CH₂C(O)OR₁ group) | 44' | (cyclopentane with OH, C(CH₃)₂OH substituent, and CH₂C(O)OR₁ group) |
| 45 | (cyclopentane with OH, p-tolyl substituent, and CH₂C(O)OR₁ group) | 45' | (cyclopentane with OH, p-tolyl substituent, and CH₂C(O)OR₁ group) |
| 46 | (cyclopentane with OH, C(O)OMe substituent, and CH₂C(O)OR₁ group) | 46' | (cyclopentane with OH, C(O)OMe substituent, and CH₂C(O)OR₁ group) |
| 47 | (cyclopentane with OH, C(O)OEt substituent, and CH₂C(O)OR₁ group) | 47' | (cyclopentane with OH, C(O)OEt substituent, and CH₂C(O)OR₁ group) |
| 48 | (cyclopentane with OH, 2-aminophenyl substituent, and CH₂C(O)OR₁ group) | 48' | (cyclopentane with OH, 2-aminophenyl substituent, and CH₂C(O)OR₁ group) |
| 49 | (cyclopentane with OH, 2-hydroxyphenyl substituent, and CH₂C(O)OR₁ group) | 49' | (cyclopentane with OH, 2-hydroxyphenyl substituent, and CH₂C(O)OR₁ group) |

TABLE 1-continued

| No. | Structure R1 = H | No. | Structure R1 = C₂H₅ |
|---|---|---|---|
| 50 | | 50' | |
| 51 | | 51' | | and also the optical isomers, diastereoisomers and/or corresponding salts thereof.

The preparation process according to the present invention also makes it possible to obtain the compounds described in all the variants presented in the remainder of the description.

The present invention also relates to the cosmetic use of at least one compound of formula (I), for promoting skin desquamation, stimulating epidermal renewal, combating the signs of skin aging, improving the radiance of the complexion and/or smoothing out facial skin,

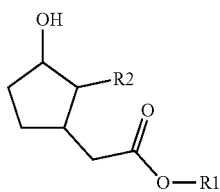

(I)

wherein R1 and R2 are as described above, and also the optical isomers, diastereoisomers and corresponding salts thereof, with the exclusion of the compounds of formula (I) for which:

when R2 is a pentyl radical, R1 is a hydrogen atom or a methyl group.

More specifically, the present invention relates to the cosmetic use of at least one compound of formula (I), for promoting skin desquamation, stimulating epidermal renewal, combating the signs of skin aging, improving the radiance of the complexion and/or smoothing out facial skin,

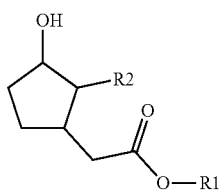

(I)

wherein R1 represents a hydrogen atom, a phenyl radical or a linear or branched, saturated or unsaturated hydrocarbon-based radical containing 1 to 8 carbon atoms, R2 denotes a radical chosen from:

a linear, branched or cyclic, saturated hydrocarbon-based radical containing 1 to 12 carbon atoms, optionally substituted with 1 to 3 groups, which may be identical or different, chosen from —OR31, —NR31R41, —COOR31, —OCOR31 and halogens, with R31 and R41 representing, independently of one another, a hydrogen atom, a phenyl radical or a linear or branched, saturated or unsaturated alkyl radical containing 1 to 4 carbon atoms;

a radical —Ar—R22 with Ar being an aromatic nucleus chosen from phenyl or pyridyl groups, and R22 representing a substituent chosen from hydrogen, —OR', —NO₂, halogens, —NH₂, —CF₃ and —R', with R' denoting a hydrogen atom, a linear, branched or cyclic, saturated or unsaturated hydrocarbon-based radical containing 1 to 6 carbon atoms, or a phenyl radical;

a radical —R23-Ph wherein R23 represents a linear or branched, saturated or unsaturated hydrocarbon-based divalent radical containing 1 to 6 carbon atoms, optionally substituted with 1 to 3 —OH groups and/or optionally interrupted with 1 to 3 non-adjacent oxygen atoms;

a radical —R24-NH—R34 with R24 representing a linear or branched, saturated or unsaturated hydrocarbon-based divalent radical containing 1 to 4 carbon atoms, optionally substituted with 1 to 3 —OH groups and/or optionally interrupted with 1 to 3 oxygen atoms; R34 representing a substituent —COOR' or a linear or branched, saturated or unsaturated hydrocarbon-based radical containing 1 to 4 carbon atoms, optionally interrupted with an NH, O or S group, with R' representing a hydrogen atom, a linear, branched or cyclic, saturated hydrocarbon-based radical containing 1 to 6 carbon atoms, or a phenyl radical;

a radical —CO—O—R25 wherein R25 represents a hydrogen atom, a phenyl radical or a linear or branched, saturated or unsaturated hydrocarbon-based radical containing 1 to 8 carbon atoms;

with the exclusion
of the compounds of formula (I) for which R2 is a pentyl radical and R1 is a hydrogen atom or a methyl group.

In particular, the compounds used in the context of the invention correspond to formula (I) for which R1 represents a hydrogen atom, a phenyl radical or a linear or branched, saturated or unsaturated hydrocarbon-based radical containing 1 to 8 carbon atoms, and R2 denotes a radical chosen from:
- a linear, branched or cyclic, saturated hydrocarbon-based radical containing from 1 to 7 or 9 to 11 carbon atoms, optionally substituted with 1 to 3 groups, which may be identical or different, chosen from —OR31, —NR31R41, —COOR31, —OCOR31 and halogens, with R31 and R41 representing, independently of one another, a hydrogen atom, a phenyl radical or a linear or branched, saturated or unsaturated alkyl radical containing 1 to 4 carbon atoms;
- a cyclic, saturated hydrocarbon-based radical containing from 5 to 7 carbon atoms, or a linear, saturated hydrocarbon-based radical containing 1, 2, 3, 4 or 6 carbon atoms, these radicals possibly being substituted with 1 to 3 groups, which may be identical or different, chosen from —OR31, —NHR31, —COOR31 and halogens, with R31 representing a hydrogen atom, a phenyl radical or a linear or branched, saturated or unsaturated alkyl radical containing 1 to 4 carbon atoms;

or the optical isomers, diastereoisomers and/or corresponding salts thereof.

The present invention also relates to the compounds of formula (I):

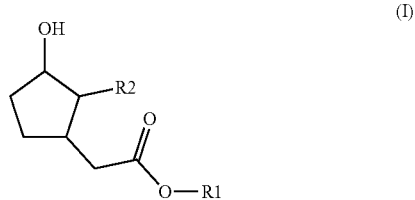

wherein R1 represents a hydrogen atom, a phenyl radical or a linear or branched, saturated or unsaturated hydrocarbon-based radical containing 1 to 8 carbon atoms, R2 denotes a radical chosen from:
- a linear, branched or cyclic, saturated hydrocarbon-based radical containing 1 to 12 carbon atoms, optionally substituted with 1 to 3 groups, which may be identical or different, chosen from —OR31, —NR31R41, —COOR31, —OCOR31 and halogens, with R31 and R41 representing, independently of one another, a hydrogen atom, a phenyl radical or a linear or branched, saturated or unsaturated alkyl radical containing 1 to 4 carbon atoms; with the exclusion of the compounds of formula (I) for which R2 is a pentyl radical and R1 is a hydrogen atom or a methyl group;
- a radical —Ar—R22 with Ar being an aromatic nucleus chosen from phenyl or pyridyl groups, and R22 representing a substituent chosen from hydrogen, —OR', —NO$_2$, halogens, —NH$_2$, —CF$_3$ and —R', with R' denoting a hydrogen atom, a linear, branched or cyclic, saturated or unsaturated hydrocarbon-based radical containing 1 to 6 carbon atoms, or a phenyl radical;
- a radical —R23-Ph wherein R23 represents a linear or branched, saturated or unsaturated hydrocarbon-based divalent radical containing 1 to 6 carbon atoms, optionally substituted with 1 to 3 —OH groups and/or optionally interrupted with 1 to 3 non-adjacent oxygen atoms; with the exclusion of the compounds

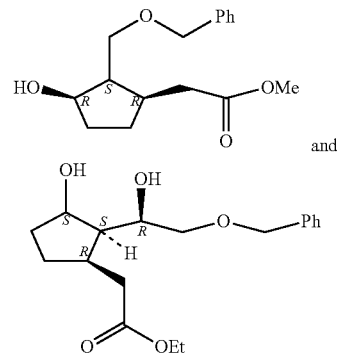

and

- a radical —R24-NH—R34 with R24 representing a linear or branched, saturated or unsaturated hydrocarbon-based divalent radical containing 1 to 4 carbon atoms, optionally substituted with 1 to 3 —OH groups and/or optionally interrupted with 1 to 3 oxygen atoms; R34 representing a substituent —COOR' or a linear or branched, saturated or unsaturated hydrocarbon-based radical containing 1 to 4 carbon atoms, optionally interrupted with an NH, O or S group, with R' representing a hydrogen atom, a linear, branched or cyclic, saturated hydrocarbon-based radical containing 1 to 6 carbon atoms, or a phenyl radical;
- a radical —CO—O—R25 wherein R25 represents a hydrogen atom, a phenyl radical or a linear or branched, saturated or unsaturated hydrocarbon-based radical containing 1 to 8 carbon atoms;

with the exclusion of the compound

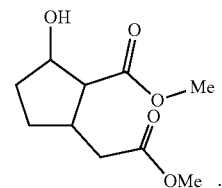 [SMILES: COC(=O)CC1CCC(O)C1C(=O)OC]

A first group of preferred compounds is chosen from the compounds of formula (I), wherein R1 is as defined above, preferably R1 is hydrogen or an ethyl group, and R2 denotes a linear, saturated hydrocarbon-based radical containing 3 to 12 carbon atoms, substituted with 1 to 3 groups, which may be identical or different, chosen from —OR31, —NHR31, —COOR31, —OCOR31 and halogens, with R31 representing a hydrogen atom, a phenyl radical or a linear or branched, saturated or unsaturated alkyl radical containing 1 to 4 carbon atoms, or R2 denotes a radical chosen from a cyclic, saturated hydrocarbon-based radical containing 5 to 7 carbon atoms, possibly substituted with 1 to 3 groups, which may be identical or different, chosen from —OR31, —NHR31, —COOR31, —OCOR31 and halogens, with R31 representing a hydrogen atom, a phenyl radical or a linear or branched, saturated or unsaturated alkyl radical containing 1 to 4 carbon atoms;

R2 denotes a branched, saturated hydrocarbon-based radical containing 3 to 12 carbon atoms, optionally substituted with 1 to 3 groups, which may be identical or different, chosen from —OR31, —NHR31, —COOR31, —OCOR31 and halogens, with R31 representing a hydrogen atom, a phenyl radical or a linear or branched, saturated or unsaturated alkyl radical containing 1 to 4 carbon atoms.

In particular, the following preferred compounds are mentioned:

A second group of preferred compounds is chosen from the compounds of formula (I), wherein R1 is as defined above, preferably R1 is hydrogen or a linear or branched, saturated hydrocarbon-based group comprising from 1 to 4 carbon atoms, preferably ethyl, and R2 is a radical —Ar—R22 with Ar being a phenyl or pyridyl aromatic nucleus and R22 represents a substituent of the aromatic nucleus Ar chosen from hydrogen, —OR', —NO$_2$, —F, —Br, —NH$_2$, —CF$_3$ and —R', with R' representing a hydro-

| No. | Structure R1 = H | No. | Structure R1 = C$_2$H$_5$ |
|---|---|---|---|
| 1 | | 40' | |
| 5 | | | |
| 6 | | 6' | |
| 7 | | 7' | |
| 11 | | 11' | | gen atom, a linear, branched or cyclic, saturated hydrocarbon-based radical containing 1 to 4 carbon atoms or a phenyl radical.

In particular, the following preferred compounds are mentioned:

| No. | Structure R1 = H | No. | Structure R1 = C$_2$H$_5$ |
|---|---|---|---|
| 12 | | 12' | |
| 13 | | 13' | |
| 14 | | 14' | |
| 15 | | 15' | |
| 16 | | 16' | |
| 17 | | 17' | |
| 18 | | 18' | |

-continued

| No. | Structure R1 = H | No. | Structure R1 = C₂H₅ |
|---|---|---|---|
| 19 | (cyclopentane with OH, 4-hydroxyphenyl, CH₂C(O)OR₁ substituents) | 19' | (cyclopentane with OH, 4-hydroxyphenyl, CH₂C(O)OR₁ substituents) |
| 20 | (cyclopentane with OH, 4-phenylphenyl, CH₂C(O)OR₁ substituents) | 20' | (cyclopentane with OH, 4-phenylphenyl, CH₂C(O)OR₁ substituents) |
| 21 | (cyclopentane with OH, 4-CF₃-phenyl, CH₂C(O)OR₁ substituents) | 21' | (cyclopentane with OH, 4-CF₃-phenyl, CH₂C(O)OR₁ substituents) |
| 22 | (cyclopentane with OH, 3-hydroxyphenyl, CH₂C(O)OR₁ substituents) | 22' | (cyclopentane with OH, 3-hydroxyphenyl, CH₂C(O)OR₁ substituents) |
| 23 | (cyclopentane with OH, 4-butylphenyl, CH₂C(O)OR₁ substituents) | 23' | (cyclopentane with OH, 4-butylphenyl, CH₂C(O)OR₁ substituents) |
| 45 | (cyclopentane with OH, 4-methylphenyl, CH₂C(O)OR₁ substituents) | 45' | (cyclopentane with OH, 4-methylphenyl, CH₂C(O)OR₁ substituents) |
| 48 | (cyclopentane with OH, 2-aminophenyl, CH₂C(O)OR₁ substituents) | 48' | (cyclopentane with OH, 2-aminophenyl, CH₂C(O)OR₁ substituents) |

| No. | Structure R1 = H | No. | Structure R1 = C₂H₅ |
|---|---|---|---|
| 49 | *(structure)* | 49' | *(structure)* |

A third group of preferred compounds is chosen from the compounds of formula (I), wherein R1 is as defined above, preferably R1 is hydrogen or a linear or branched, saturated hydrocarbon-based group comprising from 1 to 4 carbon atoms, preferably ethyl, and R2 is a radical —R23-Ph with R23 representing a linear saturated or unsaturated hydrocarbon-based radical containing 1 to 6 carbon atoms, optionally substituted with 1 to 3 —OH groups and/or optionally interrupted with 1 oxygen atom.

In particular, the following preferred compounds are mentioned:

| No. | Structure R1 = H | No. | Structure R1 = C₂H₅ |
|---|---|---|---|
| 24 | *(structure)* | 24' | *(structure)* |
| 25 | *(structure)* | 25' | *(structure)* |
| 34 | *(structure)* | 34' | *(structure)* |

| No. | Structure R1 = H | No. | Structure R1 = C₂H₅ |
|---|---|---|---|
| 35 | | 35' | |
| 38 | | 38' | |

A fourth group of preferred compounds is chosen from the compounds of formula (I), wherein R1 is as defined above, preferably R1 is hydrogen or a linear or branched, saturated hydrocarbon-based group comprising from 1 to 4 carbon atoms, preferably ethyl, and R2 is a radical —R24-NH—R34 with R24 representing a linear, saturated divalent hydrocarbon-based radical containing 1 to 4 carbon atoms and R34 representing a substituent —COOR' or a linear, saturated hydrocarbon-based radical containing 1 to 4 carbon atoms, optionally interrupted with an oxygen atom, R' representing a linear or branched, saturated hydrocarbon-based radical containing 1 to 4 carbon atoms.

In particular, the following preferred compounds are mentioned:

| No. | Structure R1 = H | No. | Structure R1 = C₂H₅ |
|---|---|---|---|
| 27 | | 27' | |
| 28 | | 28' | |
| 29 | | 29' | |

A fourth group of preferred compounds is chosen from the compounds of formula (I), wherein R1 is as defined above, preferably R1 is hydrogen or a linear or branched, saturated hydrocarbon-based group comprising from 1 to 4 carbon atoms, preferably ethyl, and R2 is a radical —CO—O—R25 and —R25 represents a hydrogen atom or a linear or branched, saturated hydrocarbon-based radical containing 1 to 4 carbon atoms.

In particular, the following preferred compounds are mentioned:

| No. | Structure R1 = H | No. | Structure R1 = C$_2$H$_5$ |
|---|---|---|---|
| 46 | cyclopentane with OH, C(=O)OMe, CH$_2$C(=O)OR$_1$ | 46' | cyclopentane with OH, C(=O)OMe, CH$_2$C(=O)OR$_1$ |
| 47 | cyclopentane with OH, C(=O)OEt, CH$_2$C(=O)OR$_1$ | 47' | cyclopentane with OH, C(=O)OEt, CH$_2$C(=O)OR$_1$ |

The present invention also relates to a composition, in particular a cosmetic composition, comprising at least one compound according to the invention.

The amount of compound of formula (I) that may be used in the composition according to the invention obviously depends on the desired effect and must be an amount that is effective for promoting desquamation of the skin and/or for stimulating epidermal renewal and thus combating intrinsic and/or extrinsic aging of the skin.

By way of example, the amount of compound of formula (I) that may be used according to the invention may range, for example, from 0.001% to 20%, preferably from 0.1% to 10% and in particular from 0.5% to 5% by weight relative to the total weight of the composition.

The composition comprising the compounds according to the invention, alone or in a mixture, may comprise moreover a physiologically acceptable medium, that is to say a medium that is compatible with all keratin materials such as the skin, the scalp, the nails, the mucous membranes, the eyes and the hair, or any other area of bodily skin. This composition may be a cosmetic composition and may thus comprise a cosmetically acceptable medium.

The physiologically acceptable medium may comprise water, organic solvents such as a $C_1$-$C_8$ alcohol, in particular ethanol, isopropanol, tert-butanol or n-butanol; a polyol such as glycerol; a glycol such as butylene glycol, isoprene glycol, propylene glycol, pentylene glycol or polyethylene glycols such as PEG-8; polyol ethers.

The composition may also comprise a fatty phase, which may comprise oils, gums and waxes normally used in the field of application under consideration. As oils or waxes that can be used in the invention, mention may be made of mineral oils, vegetable oils, animal oils, synthetic oils, silicone oils or waxes and fluoro oils, $C_{12}$-$C_{30}$ fatty alcohols, $C_{12}$-$C_{30}$ fatty acids and $C_{12}$-$C_{50}$ fatty esters.

When the composition is an emulsion, the proportion of the fatty phase may range from 0.1% to 80% by weight and preferably from 5% to 50% by weight relative to the total weight of the composition. The oils, waxes, emulsifiers and co-emulsifiers used in the composition in emulsion form are chosen from those conventionally used in cosmetics. The emulsifier and the co-emulsifier are present in the composition in a proportion ranging from 0.3% to 30% by weight and preferably from 0.5% to 20% by weight relative to the total weight of the composition. The emulsion may also contain lipid vesicles.

The composition may also contain cosmetic adjuvants that are common in the field in question, such as surfactants, emulsifiers, hydrophilic or lipophilic gelling agents, hydrophilic or lipophilic additives, preserving agents, antioxidants, solvents, fragrances, fillers, screening agents, odor absorbers, colorants and cosmetic active agents. The amounts of these various adjuvants are those conventionally used in the cosmetics field, and are, for example, from 0.01% to 10% of the total weight of the composition. Depending on their nature, these adjuvants may be introduced into the fatty phase and/or into the aqueous phase.

Among the hydrophilic active agents, mention may be made of proteins or protein hydrolyzates, amino acids, polyols, urea, allantoin, sugars and sugar derivatives, water-soluble vitamins, plant extracts and hydroxy acids.

As lipophilic active agents, mention may be made of retinol (vitamin A) and derivatives thereof, tocopherol (vitamin E) and derivatives thereof, essential fatty acids, ceramides, essential oils, and salicylic acid and derivatives thereof.

According to the invention, the composition may combine at least one compound of formula (I) with other active agents, such as:

agents which improve hair regrowth and/or slow down hair loss, agents which promote hair regrowth;
agents which modulate skin differentiation and/or proliferation and/or pigmentation;
antibacterial agents;
antiparasitics;
antifungal agents;
antiviral agents;
steroidal and non-steroidal anti-inflammatories;
anesthetics;
antipruritic agents;
keratolytic agents;
free-radical scavengers;
antiseborrheics;
antidandruff agents;
antiacne agents;
extracts of plant, marine or bacterial origin.

The composition can be provided in all the formulation forms which can be envisaged.

In particular, the composition may be in the form of an aqueous, alcoholic, aqueous-alcoholic or oily solution; a dispersion of the lotion or serum type; water-in-oil, oil-in-water or multiple emulsions; a suspension; microcapsules or microparticles; vesicular dispersions of ionic and/or nonionic type; an aqueous or oily lotion or a lotion in serum form; capsules, granules, syrups or tablets; foams, solid preparations; an aerosol composition also comprising a propellant under pressure.

The composition may be in the form of a cleansing, protecting, treating or care composition for the face, the hands, the feet, the major anatomical folds or the body, for example, day cream, night cream, makeup-removing cream, antisun composition, protective or care body milk, aftersun milk, lotion, gel or foam for caring for the skin, such as cleansing lotions, or artificial tanning compositions; a composition for making up the body or face, such as a foundation; a bath composition; a deodorizing composition comprising, for example, a bactericidal agent; an aftershave composition; a hair-removing composition; an insect bite repellent composition.

The composition according to the invention finds a most particular application as a cosmetic composition intended for the care of the skin of the body, the face and/or the scalp, in particular for promoting skin desquamation, stimulating epidermal renewal, combating the signs of skin aging, improving the radiance of the complexion and/or smoothing out facial skin.

The examples that follow illustrate the invention without limiting its scope.

EXAMPLES

I. Preparation of the Compounds

Example 1: Preparation of Compound 5

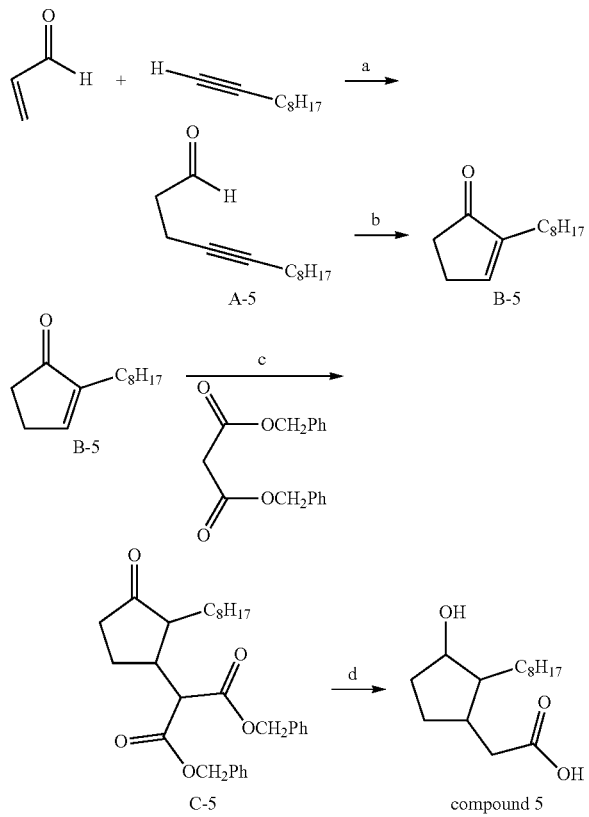

Step a:

A 1 M solution of $PMe_3$ in toluene (0.30 equiv., 0.15 mmol, 1 ml) is added to $Pd(OAc)_2$ (0.1 equiv., 0.05 mmol, 11.2 mg). The mixture is heated at 110° C. under argon for 10 min, in such a way that $Pd(OAc)_2$ is completely dissolved. After a return to ambient temperature, the reaction medium is diluted by adding 0.5 ml of water and then a mixture of 1-decyne (1 equiv., 0.5 mmol) and acrolein (5 equiv., 2.5 mmol) is added. The mixture is heated at 60° C. for 17 h (complete disappearance of the 1-decyne by TLC). After a return to ambient temperature, the reaction mixture is diluted in diethyl ether and the phases are separated. The aqueous phase is extracted 3 times with diethyl ether and then the organic phases are combined, dried over $MgSO_4$ and concentrated under reduced pressure. The residue is purified by silica gel column chromatography (hexane/ethyl acetate: 95/5) in order to isolate the intermediate A-5 with a yield of 62%.

Step b:

The intermediate A-5 is cyclized by a rhodium-catalyzed intramolecular hydroacylation reaction according to the conditions described by Tanaka and Fu (J. Am. Chem. Soc. 2001, 123, 11492) for this type of reaction.

The complex of rhodium $[Rh(dppe)]_2(BF_4)_2$ (0.1 equiv.) and the intermediate A-5 (1 equiv.) are dissolved in acetone in a Schlenk tube, under an inert atmosphere. The tube is sealed and the reaction mixture is stirred at a temperature of 90° C. for 16 h. After a return to ambient temperature, acetonitrile is added and the solvents are evaporated off under reduced pressure. The residue is purified by silica gel column chromatography in order to isolate the intermediate B-5.

Step c:

5 equivalents of the malonate derivative $CH_2(CO_2CH_2Ph)(CO_2CH_2Ph)$ are dissolved in THF.

The malonate derivative is then treated, at a temperature between −78° C. and 30° C., with 5 equivalents of a strong base: magnesium diethanolate.

The reaction medium is stirred for 30 min, then 1 equivalent of the cyclopentenone B-5, dissolved beforehand in the reaction solvent, is added dropwise.

The reaction mixture is stirred for 4 h and then cooled to a temperature of between −30 and 0° C. The excess base is neutralized by adding a saturated aqueous $NH_4Cl$ solution and the adduct C-5 is extracted 3 times using ethyl acetate. The organic phases are combined, dried over $Na_2SO_4$ and concentrated under reduced pressure. The residue is purified by silica gel column chromatography in order to isolate the intermediate C-5.

Step d:

The intermediate C-5, dissolved beforehand in ethanol, is stirred at a temperature between 18 and 100° C., under an atmosphere of dihydrogen in the presence of a palladium-on-carbon catalyst, for 4 h. The hydrogen is then removed by passage of an argon stream and the mixture is heated at 150° C. for 4 hours. After a return to ambient temperature, the hydrogenation catalyst is filtered off through celite. The filtrate is concentrated under reduced pressure and the residue is purified by silica gel column chromatography in order to isolate the compound 5.

Example 2: Preparation of Compound 9

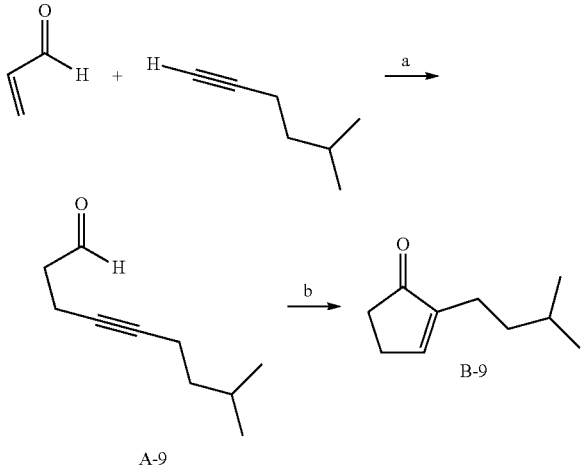

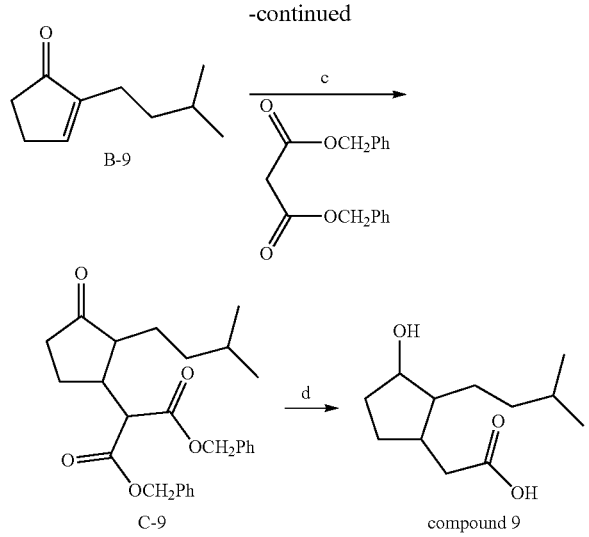

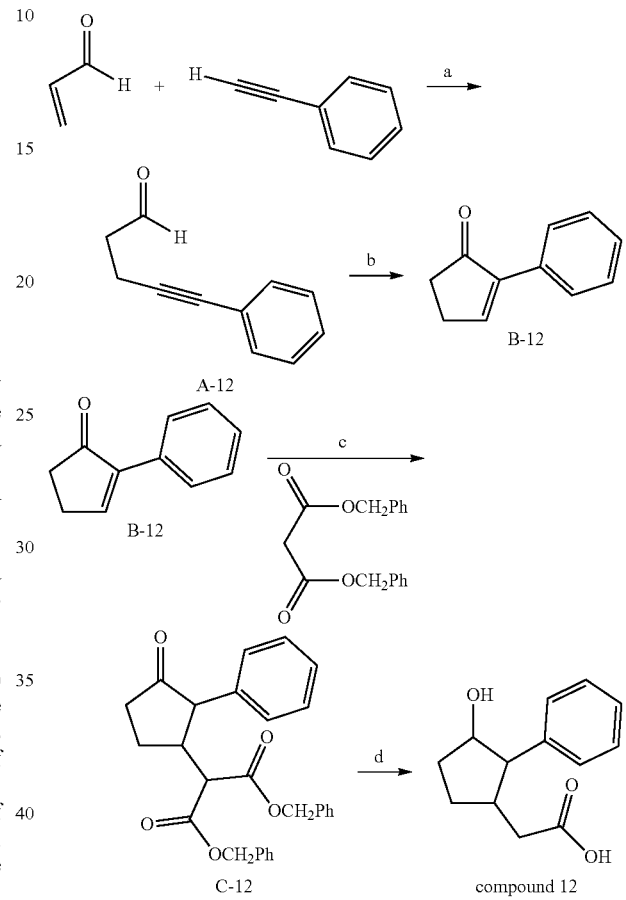

Example 3: Preparation of Compound 12

Step a:

The intermediate A-9 is obtained in a manner strictly similar to the intermediate A-5, by substituting the 1-decyne with 5-methylhex-1-yne, with a reaction time of 17 h. Yield 51%.

The $^1$H NMR spectrum and the mass spectrum are in accordance with the expected structure.

Step b:

The intermediate A-9 is cyclized by a rhodium-catalyzed intramolecular hydroacylation reaction according to the conditions described by Tanaka and Fu (J. Am. Chem. Soc. 2001, 123, 11492) for this type of reaction.

The complex of rhodium [Rh(dppe)]$_2$(BF$_4$)$_2$ (0.1 equiv.) and the intermediate A-9 (1 equiv.) are dissolved in acetone in a Schlenk tube, under an inert atmosphere. The tube is sealed and the reaction mixture is stirred at a temperature of 90° C. for 16 h. After a return to ambient temperature, acetonitrile is added and the solvents are evaporated off under reduced pressure. The residue is purified by silica gel column chromatography in order to isolate the intermediate B-9.

Step c:

5 equivalents of the malonate derivative CH$_2$(CO$_2$CH$_2$Ph)(CO$_2$CH$_2$Ph) are dissolved in THF.

The malonate derivative is then treated, at a temperature between −78° C. and 30° C., with 5 equivalents of a strong base: magnesium diethanolate.

The reaction medium is stirred for 30 min, then 1 equivalent of the cyclopentenone B-9, dissolved beforehand in the reaction solvent, is added dropwise.

The reaction mixture is stirred for 4 h and then cooled to a temperature of between −30 and 0° C. The excess base is neutralized by adding a saturated aqueous NH$_4$Cl solution and the adduct C-9 is extracted 3 times using ethyl acetate. The organic phases are combined, dried over Na$_2$SO$_4$ and concentrated under reduced pressure. The residue is purified by silica gel column chromatography in order to isolate the intermediate C-9.

Step d:

The intermediate C-9, dissolved beforehand in ethanol, is stirred at a temperature between 18 and 100° C., under an atmosphere of dihydrogen in the presence of a palladium-on-carbon catalyst, for 4 h. The hydrogen is then removed by passage of an argon stream and the mixture is heated at 150° C. for 4 hours. After a return to ambient temperature, the hydrogenation catalyst is filtered off through celite. The filtrate is concentrated under reduced pressure and the residue is purified by silica gel column chromatography in order to isolate the compound 9.

Example 3: Preparation of Compound 12

Step a:

The intermediate A-12 is obtained in a manner strictly similar to the intermediate A-5, by substituting the 1-decyne with phenylacetylene, with a reaction time of 3 h. Yield 70%.

The $^1$H NMR spectrum and the mass spectrum are in accordance with the expected structure.

Step b:

The intermediate A-12 is cyclized by a rhodium-catalyzed intramolecular hydroacylation reaction according to the conditions described by Tanaka and Fu (J. Am. Chem. Soc. 2001, 123, 11492) for this type of reaction.

The complex of rhodium [Rh(dppe)]$_2$(BF$_4$)$_2$ (0.1 equiv.) and the intermediate A-12 (1 equiv.) are dissolved in acetone in a Schlenk tube, under an inert atmosphere. The tube is sealed and the reaction mixture is stirred at a temperature of 90° C. for 16 h. After a return to ambient temperature, acetonitrile is added and the solvents are evaporated off under reduced pressure. The residue is purified by silica gel column chromatography in order to isolate the intermediate B-12 (yield 31%).

Step c:

5 equivalents of the malonate derivative CH$_2$(CO$_2$CH$_2$Ph)(CO$_2$CH$_2$Ph) are dissolved in THF.

The malonate derivative is then treated, at a temperature between −78° C. and 30° C., with 5 equivalents of a strong base: magnesium diethanolate.

The reaction medium is stirred for 30 min, then 1 equivalent of the cyclopentenone B-12, dissolved beforehand in the reaction solvent, is added dropwise.

The reaction mixture is stirred for 4 h and then cooled to a temperature of between −30 and 0° C. The excess base is neutralized by adding a saturated aqueous NH$_4$Cl solution and the adduct C-12 is extracted 3 times using ethyl acetate. The organic phases are combined, dried over Na$_2$SO$_4$ and concentrated under reduced pressure. The residue is purified by silica gel column chromatography in order to isolate the intermediate C-12.

Step d:

The intermediate C-12, dissolved beforehand in ethanol, is stirred at a temperature between 18 and 100° C., under an atmosphere of dihydrogen in the presence of a palladium-on-carbon catalyst, for 4 h. The hydrogen is then removed by passage of an argon stream and the mixture is heated at 150° C. for 4 hours. After a return to ambient temperature, the hydrogenation catalyst is filtered off through celite. The filtrate is concentrated under reduced pressure and the residue is purified by silica gel column chromatography in order to isolate the compound 12.

Example 4: Preparation of Compound 13

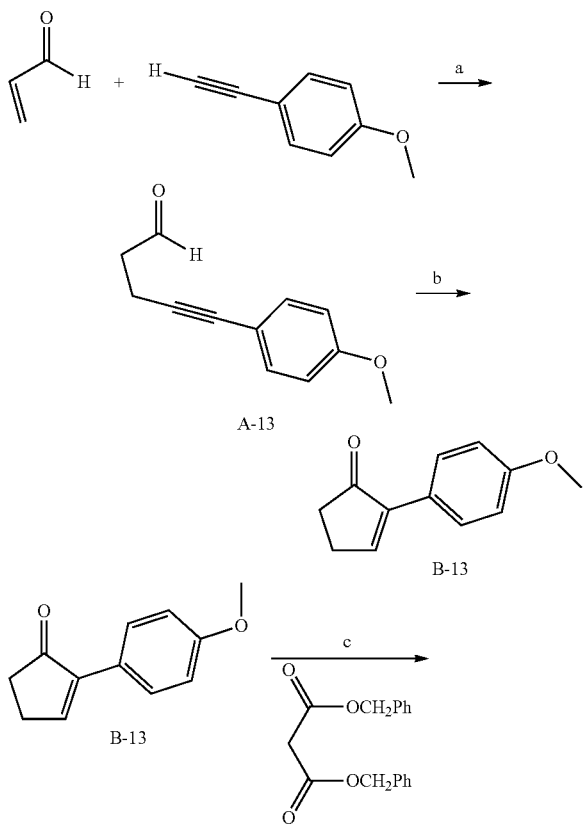

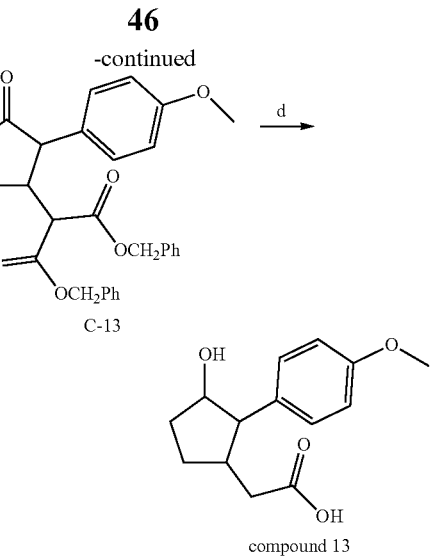

Step a:

The intermediate A-13 is obtained in a manner strictly similar to the intermediate A-5, by substituting the 1-decyne with (4-methoxyphenyl)acetylene, with a reaction time of 3 h. Yield 73%.

The $^1$H NMR spectrum and the mass spectrum are in accordance with the expected structure.

Step b:

The intermediate A-13 is cyclized by a rhodium-catalyzed intramolecular hydroacylation reaction according to the conditions described by Tanaka and Fu (J. Am. Chem. Soc. 2001, 123, 11492) for this type of reaction.

The complex of rhodium [Rh(dppe)]$_2$(BF$_4$)$_2$ (0.1 equiv.) and the intermediate A-13 (1 equiv.) are dissolved in acetone in a Schlenk tube, under an inert atmosphere. The tube is sealed and the reaction mixture is stirred at a temperature of 90° C. for 16 h. After a return to ambient temperature, acetonitrile is added and the solvents are evaporated off under reduced pressure. The residue is purified by silica gel column chromatography in order to isolate the intermediate B-13.

Step c:

5 equivalents of the malonate derivative CH$_2$(CO$_2$CH$_2$Ph)(CO$_2$CH$_2$Ph) are dissolved in THF.

The malonate derivative is then treated, at a temperature between −78° C. and 30° C., with 5 equivalents of a strong base: magnesium diethanolate.

The reaction medium is stirred for 30 min, then 1 equivalent of the cyclopentenone B-13, dissolved beforehand in the reaction solvent, is added dropwise.

The reaction mixture is stirred for 4 h and then cooled to a temperature of between −30 and 0° C. The excess base is neutralized by adding a saturated aqueous NH$_4$Cl solution and the adduct C-13 is extracted 3 times using ethyl acetate. The organic phases are combined, dried over Na$_2$SO$_4$ and concentrated under reduced pressure. The residue is purified by silica gel column chromatography in order to isolate the intermediate C-13.

Step d:

The intermediate C-13, dissolved beforehand in ethanol, is stirred at a temperature between 18 and 100° C., under an atmosphere of dihydrogen in the presence of a palladium-on-carbon catalyst, for 4 h. The hydrogen is then removed by passage of an argon stream and the mixture is heated at 150° C. for 4 hours. After a return to ambient temperature, the hydrogenation catalyst is filtered off through celite. The filtrate is concentrated under reduced pressure and the residue is purified by silica gel column chromatography in order to isolate the compound 13.

Example 5: Preparation of Compound 21

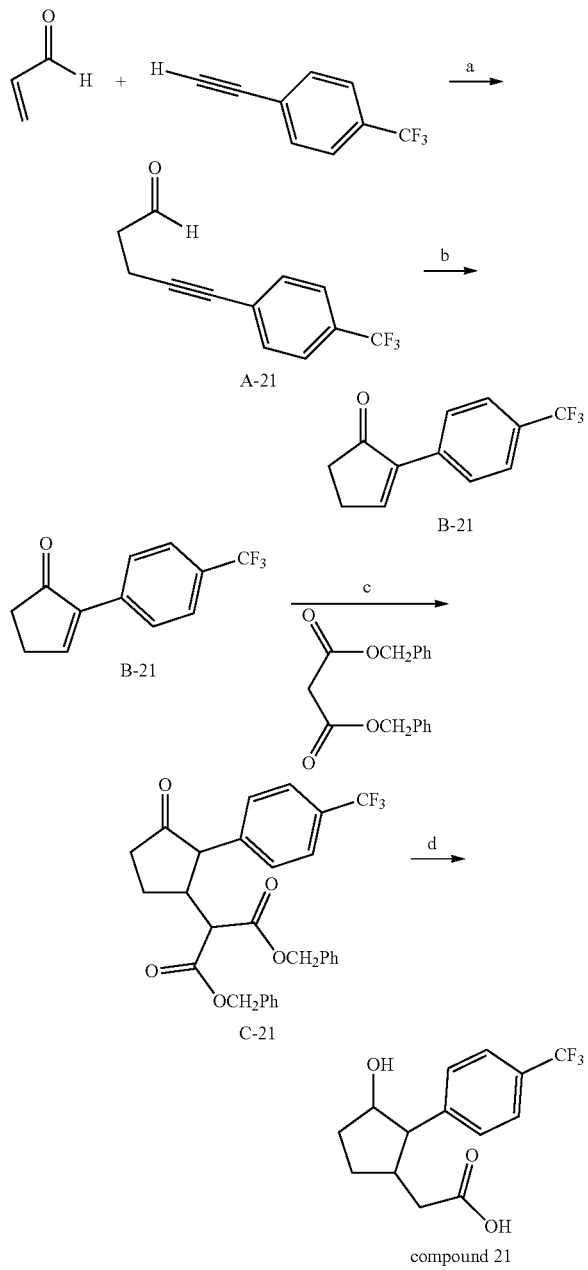

compound 21

Step a:

The intermediate A-21 is obtained in a manner strictly similar to the intermediate A-5, by substituting the 1-decyne with ((4-trifluoromethyl)phenyl)acetylene, with a reaction time of 17 h. Yield 38%.

The $^1$H NMR spectrum and the mass spectrum are in accordance with the expected structure.

Step b:

The intermediate A-21 is cyclized by a rhodium-catalyzed intramolecular hydroacylation reaction according to the conditions described by Tanaka and Fu (J. Am. Chem. Soc. 2001, 123, 11492) for this type of reaction.

The complex of rhodium [Rh(dppe)]$_2$(BF$_4$)$_2$ (0.1 equiv.) and the intermediate A-21 (1 equiv.) are dissolved in acetone in a Schlenk tube, under an inert atmosphere. The tube is sealed and the reaction mixture is stirred at a temperature of 90° C. for 16 h. After a return to ambient temperature, acetonitrile is added and the solvents are evaporated off under reduced pressure. The residue is purified by silica gel column chromatography in order to isolate the intermediate B-21.

Step c:

5 equivalents of the malonate derivative CH$_2$(CO$_2$CH$_2$Ph)(CO$_2$CH$_2$Ph) are dissolved in THF.

The malonate derivative is then treated, at a temperature between −78° C. and 30° C., with 5 equivalents of a strong base: magnesium diethanolate.

The reaction medium is stirred for 30 min, then 1 equivalent of the cyclopentenone B-21, dissolved beforehand in the reaction solvent, is added dropwise.

The reaction mixture is stirred for 4 h and then cooled to a temperature of between −30 and 0° C. The excess base is neutralized by adding a saturated aqueous NH$_4$Cl solution and the adduct C-21 is extracted 3 times using ethyl acetate. The organic phases are combined, dried over Na$_2$SO$_4$ and concentrated under reduced pressure. The residue is purified by silica gel column chromatography in order to isolate the intermediate C-21.

Step d:

The intermediate C-21, dissolved beforehand in ethanol, is stirred at a temperature between 18 and 100° C., under an atmosphere of dihydrogen in the presence of a palladium-on-carbon catalyst, for 4 h. The hydrogen is then removed by passage of an argon stream and the mixture is heated at 150° C. for 4 hours. After a return to ambient temperature, the hydrogenation catalyst is filtered off through celite. The filtrate is concentrated under reduced pressure and the residue is purified by silica gel column chromatography in order to isolate the compound 21.

Example 6: Preparation of Compound 38

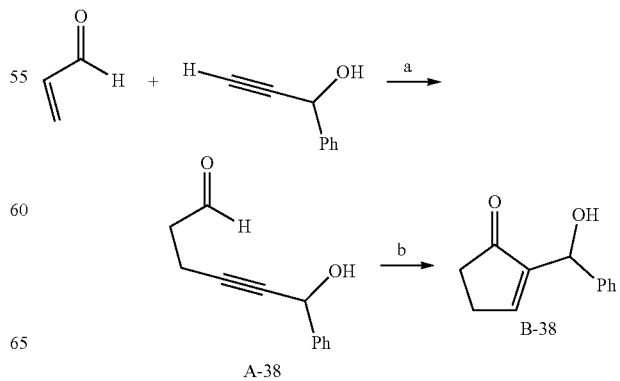

49

-continued

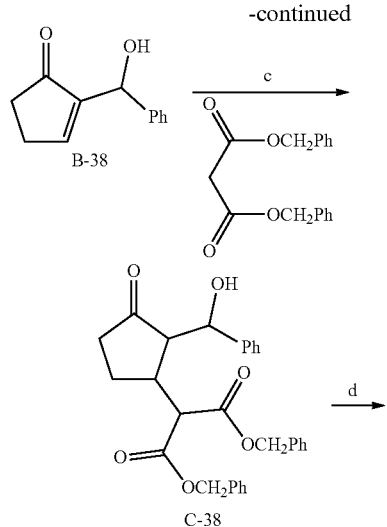

Step a:

The intermediate A-38 is obtained in a manner strictly similar to the intermediate A-5, by substituting the 1-decyne with 1-hydroxy-1-phenylprop-2-yne, with a reaction time of 3 h. Yield 43%.

The $^1$H NMR spectrum and the mass spectrum are in accordance with the expected structure.

Step b:

The intermediate A-38 is cyclized by a rhodium-catalyzed intramolecular hydroacylation reaction according to the conditions described by Tanaka and Fu (J. Am. Chem. Soc. 2001, 123, 11492) for this type of reaction.

The complex of rhodium $[Rh(dppe)]_2(BF_4)_2$ (0.1 equiv.) and the intermediate A-38 (1 equiv.) are dissolved in acetone in a Schlenk tube, under an inert atmosphere. The tube is sealed and the reaction mixture is stirred at a temperature of 90° C. for 16 h. After a return to ambient temperature, acetonitrile is added and the solvents are evaporated off under reduced pressure. The residue is purified by silica gel column chromatography in order to isolate the intermediate B-38.

Step c:

5 equivalents of the malonate derivative $CH_2(CO_2CH_2Ph)(CO_2CH_2Ph)$ are dissolved in THF.

The malonate derivative is then treated, at a temperature between −78° C. and 30° C., with 5 equivalents of a strong base: magnesium diethanolate.

The reaction medium is stirred for 30 min, then 1 equivalent of the cyclopentenone B-38, dissolved beforehand in the reaction solvent, is added dropwise.

The reaction mixture is stirred for 4 h and then cooled to a temperature of between −30 and 0° C. The excess base is neutralized by adding a saturated aqueous NH$_4$Cl solution and the adduct C-38 is extracted 3 times using ethyl acetate. The organic phases are combined, dried over Na$_2$SO$_4$ and concentrated under reduced pressure. The residue is purified by silica gel column chromatography in order to isolate the intermediate C-38.

Step d:

The intermediate C-38, dissolved beforehand in ethanol, is stirred at a temperature between 18 and 100° C., under an atmosphere of dihydrogen in the presence of a palladium-on-carbon catalyst, for 4 h. The hydrogen is then removed by passage of an argon stream and the mixture is heated at 150° C. for 4 hours. After a return to ambient temperature, the

50 hydrogenation catalyst is filtered off through celite. The filtrate is concentrated under reduced pressure and the residue is purified by silica gel column chromatography in order to isolate the compound 38.

Example 7: Preparation of Compound 1

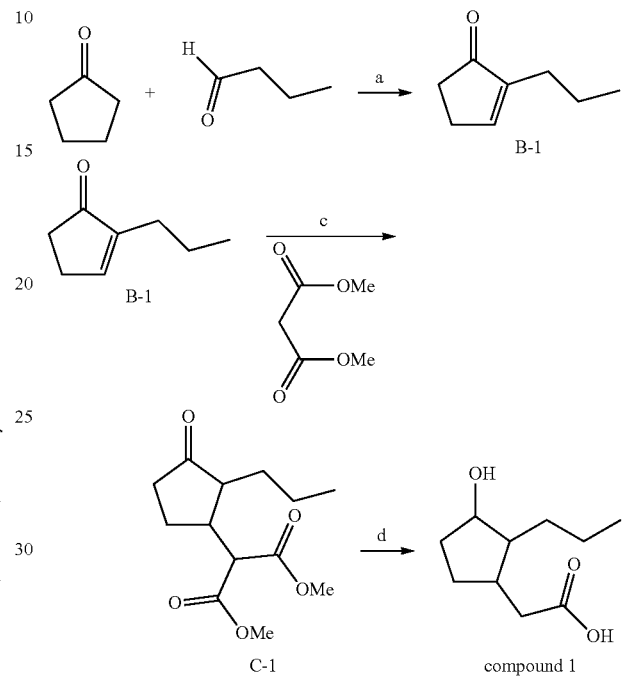

Step a:

The intermediate B-1 (CAS: 24105-07-5) is obtained in a manner known to those skilled in the art by condensation between cyclopentanone and butyraldehyde in a basic medium. Yield 60%.

The $^1$H NMR spectrum and the mass spectrum are in accordance with the expected structure.

Step c:

5 equivalents of the malonate derivative $CH_2(CO_2Me)(CO_2Me)$ are dissolved in methanol.

The malonate derivative is then treated, at 23° C., with 5 equivalents of a strong base: sodium methanolate.

The reaction medium is stirred for 6 hours, then 1 equivalent of the cyclopentenone B-1, dissolved beforehand in the reaction solvent, is added dropwise.

The reaction mixture is stirred for 4 hours. The excess base is neutralized by adding a saturated aqueous NH$_4$Cl solution and the adduct C-1 is extracted 3 times using ethyl acetate. The organic phases are combined, dried over Na$_2$SO$_4$ and concentrated under reduced pressure. The residue is purified by silica gel column chromatography in order to isolate the intermediate C-1 (yield 95%).

Step d:

The intermediate C-1, dissolved beforehand in methanol, is stirred at 23° C. in the presence of sodium borohydride, or under an atmosphere of dihydrogen in the presence of a palladium-on-carbon catalyst, for 4 h. Once this part of the reaction has ended and the reaction crude has been treated, the mixture is heated at 150° C. for 4 hours in DMSO. The filtrate is concentrated under reduced pressure and the residue is purified by silica gel column chromatography in order to isolate the compound 1 (40% yield).

The $^1$H NMR spectrum and the mass spectrum are in accordance with the expected structure.

II. Epidermal Renewal and Barrier Effect

The influence of compound 5, in particular obtained according to the preparation process described in example 1 above, on the epidermal renewal and the barrier effect of the skin was evaluated in vitro by measuring the expression of the TGM1 and TGM3 transcripts in keratinocytes.

Transglutaminase is an aminoacyltransferase. It is in the form of generally water-insoluble protein polymers. These biological polymers are essential to the body for creating stable barriers and structures. Thus, transglutaminase is involved, inter alia, in skin and hair synthesis. In particular, transglutaminase 3 (TGM3) is an epidermal transglutaminase (cf Griffin et al. Biochem. J. 2002, vol. 368, 377-396).

Protocol

Human epidermal keratinocytes were incubated for 24 hours in the presence or absence (control) of the compound to be tested. At the end of the incubation, the total RNAs were extracted and then quantified. The expression of the TGM1 and TGM3 transcripts was then measured by means of a 2-step RT-qPCR method by means of a LightCycler® 480 system and according to the SYBR®Green (Qiagen) incorporation technique. The expression of these transcripts was standardized relative to the expression of 2 housekeeping genes, RPL13A and GAPDH. The experiment was reproduced 3 times (N=3).

TABLE 2 characteristics of the primers used for the quantitative PCR step:

| Gene | Abbreviation | Gene ID | Name Qiagen | Ref QIAGEN |
|---|---|---|---|---|
| Transglutaminase 1 | TGM1 | 7051 | Hs_TGM1_1_SG QuantiTect Primer Assay | QT00082320 |
| Transglutaminase 3 | TGM3 | 7053 | Hs_TGM3_1_SG QuantiTect Primer Assay | QT00001295 |
| Glyceraldehyde 3-phosphate dehydrogenase | GAPDH | 2597 | HS_GAPDH_2_SG QuantiTect Primer Assay | QT01192646 |
| 60S ribosomal protein L13A | RPL13A | 23521 | Hs_RPL13A_2_SG QuantiTect Primer Assay | QT02321333 |

Results

The results are expressed as fold change (fc) relative to the control.

Moderate stimulation: 1.5<fc<2
Clear stimulation: 2<fc<3
Strong simulation: fc>3
Moderate inhibition: 0.5<fc<0.7
Clear inhibition: fc<0.5

| | compound 5 (100 µm) |
|---|---|
| TGM1 | 1.9 |
| TGM3 | 1.8 |

Compound 5 (at 100 µm) moderately stimulated the expression of the TGM1 and TGM3 transcripts.

These results show that compound 5 according to the invention has a significant effect on increasing the expression of the TGM1 and TGM3 transglutaminases.

This increase in transglutaminase expression reflects a reinforcement of the horny layer of the epidermis and also an improvement in the barrier function, making it possible to delay withering and thinning of the skin.

These results show an anti-aging effect of compound 5 on the skin, in particular by reinforcement of the barrier function.

The invention claimed is:

1. A process for preparing a compound of formula (I):

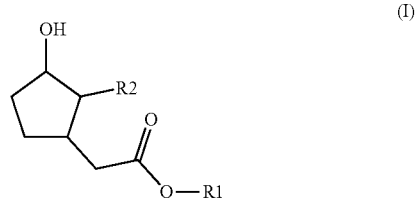

wherein R1 represents a hydrogen atom, a phenyl radical or a linear or branched, saturated or unsaturated hydrocarbon-based radical containing 1 to 8 carbon atoms, R2 denotes a radical chosen from:

a linear, branched or cyclic, saturated hydrocarbon-based radical containing 1 to 12 carbon atoms, optionally substituted with 1 to 3 groups, which may be identical or different, chosen from —OR31, —NR31R41, —COOR31, —OCOR31 and halogens, with R31 and R41 representing, independently of one another, a hydrogen atom, a phenyl radical or a linear or branched, saturated or unsaturated alkyl radical containing 1 to 4 carbon atoms;

a radical —Ar—R22 with Ar being an aromatic nucleus chosen from phenyl or pyridyl groups, and R22 representing a substituent chosen from hydrogen, —OR', —NO$_2$, halogens, —NH$_2$, —CF$_3$ and —R', with R' denoting a hydrogen atom, a linear, branched or cyclic, saturated or unsaturated hydrocarbon-based radical containing 1 to 6 carbon atoms, or a phenyl radical;

a radical —R23-Ph wherein R23 represents a linear or branched, saturated or unsaturated hydrocarbon-based divalent radical containing 1 to 6 carbon atoms, optionally substituted with 1 to 3 —OH groups and/or optionally interrupted with 1 to 3 non-adjacent oxygen atoms;

a radical —R24-NH—R34 with R24 representing a linear or branched, saturated or unsaturated hydrocarbon-based divalent radical containing 1 to 4 carbon atoms, optionally substituted with 1 to 3 —OH groups and/or optionally interrupted with 1 to 3 oxygen atoms; R34 representing a substituent —COOR' or a linear or branched, saturated or unsaturated hydrocarbon-based radical containing 1 to 4 carbon atoms, optionally interrupted with an NH, O or S group, with R' representing a hydrogen atom, a linear, branched or cyclic, saturated hydrocarbon-based radical containing 1 to 6 carbon atoms, or a phenyl radical;

a radical —CO—O—R25 wherein R25 represents a hydrogen atom, a phenyl radical or a linear or branched, saturated or unsaturated hydrocarbon-based radical containing 1 to 8 carbon atoms;

and also the optical isomers, diastereoisomers and/or corresponding salts thereof;

in which process the following steps are carried out:
a) 1,4 addition to acrolein of an alkyne of formula R2C≡H with R2 as defined in formula (I) above;
b) cyclization of the product obtained at the end of step a) by intramolecular hydroacylation;
c) 1,4 addition to the cyclopentenone resulting from step b) of the malonate derivative CH$_2$(CO$_2$CH$_2$Ph)(CO$_2$R0) for which, when in formula (I) R1 is a hydrogen atom, then —R0 is —CH$_2$Ph and when in formula (I) R1 is not a hydrogen atom, then R0 is R1;
d) reduction and decarboxylation of the product obtained in step c).

2. The process as claimed in claim 1 for preparing a compound of formula (I), wherein R1 is as defined in claim 1, and
R2 denotes a linear, saturated hydrocarbon-based radical containing 3 to 12 carbon atoms, substituted with 1 to 3 groups, which may be identical or different, chosen from —OR31, —NHR31, —COOR31, —OCOR31 and halogens, with R31 representing a hydrogen atom, a phenyl radical or a linear or branched, saturated or unsaturated alkyl radical containing 1 to 4 carbon atoms, or
R2 denotes a radical chosen from a cyclic, saturated hydrocarbon-based radical containing 5 to 7 carbon atoms, possibly substituted with 1 to 3 groups, which may be identical or different, chosen from —OR31, —NHR31, —COOR31, —OCOR31 and halogens, with R31 representing a hydrogen atom, a phenyl radical or a linear or branched, saturated or unsaturated alkyl radical containing 1 to 4 carbon atoms;
R2 denotes a branched, saturated hydrocarbon-based radical containing 3 to 12 carbon atoms, optionally substituted with 1 to 3 groups, which may be identical or different, chosen from —OR31, —NHR31, —COOR31, —OCOR31 and halogens, with R31 representing a hydrogen atom, a phenyl radical or a linear or branched, saturated or unsaturated alkyl radical containing 1 to 4 carbon atoms.

3. The process as claimed in claim 1, wherein the compound of formula (I) is chosen from the following compounds:

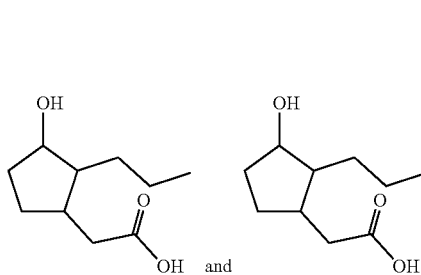

4. The process as claimed in claim 1 for preparing a compound of formula (I), wherein R1 is as defined in claim 1, and R2 denotes a radical —Ar—R22 with Ar being a phenyl or pyridyl aromatic nucleus and
R22 represents a substituent of the aromatic nucleus Ar chosen from hydrogen, —OR', —NO$_2$, —F, —Br, —NH$_2$, —CF$_3$ and —R', with R' representing a hydrogen atom, a linear, branched or cyclic, saturated hydrocarbon-based radical containing 1 to 4 carbon atoms or a phenyl radical.

5. The process as claimed in claim 1 for preparing a compound of formula (I), wherein R1 is as defined in claim 1, and R2 is a radical —R23Ph with R23 representing a linear saturated or unsaturated hydrocarbon-based radical containing 1 to 6 carbon atoms, optionally substituted with 1 —OH group and/or optionally interrupted with 1 oxygen atom, with the exclusion of the compounds

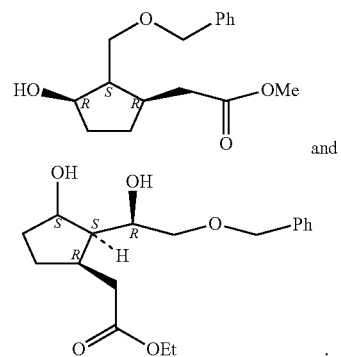

6. The process as claimed in claim 1 for preparing a compound of formula (I), wherein R1 is as defined in claim 1, and R2 is a radical —R24-NH—R34 with R24 representing a linear, saturated divalent hydrocarbon-based radical containing 1 to 4 carbon atoms and R34 representing a substituent —COOR' or a linear saturated hydrocarbon-based radical containing 1 to 4 carbon atoms, optionally interrupted with an oxygen atom, R' representing a linear or branched, saturated hydrocarbon-based radical containing 1 to 4 carbon atoms.

7. The process as claimed in claim 1 for preparing a compound of formula (I), wherein R1 is as defined in claim 1, and R2 is a radical —CO—O—R25 and —R25 represents a hydrogen atom or a linear or branched, saturated hydrocarbon-based radical containing 1 to 4 carbon atoms, with the exclusion of the compound

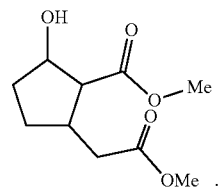 [SMILES: COC(=O)CC1CCC(O)C1C(=O)OC]

8. The process as claimed in claim 1, wherein step a) is carried out in the presence of a catalyst which is a palladium complex.

9. The process as claimed in claim 1, wherein step a) is carried out in the presence of a catalyst chosen from Pd(OAc)$_2$, Pd(TFA)$_2$, Pd(OPiv)$_2$, PdCl$_2$ and Pd$_2$dba$_3$ optionally combined with a phosphine or a rhodium complex optionally combined with a phosphine.

10. The process as claimed in claim 1, wherein, in step a), the alkyne and the acrolein are heated to a temperature of between 30° C. and 140° C. in an organic solvent.

11. The process as claimed in claim 1, wherein step a) is carried out in the presence of a catalyst which is Pd(OAc)$_2$ combined with a phosphine of formula PMe$_3$, brought into contact in a Pd(OAc)$_2$/PMe$_3$ mole ratio of approximately 1/3.

12. The process as claimed in claim 1, wherein, in step a), the alkyne and the acrolein are heated to a temperature of between 30° C. and 140° C. in an organic solvent which is a mixture of at least 2 miscible or immiscible solvents chosen from toluene, benzene, water, methanol, ethanol, isopropanol, acetone, methyl ethyl ketone, THF, Me-THF, diethyl ether, diisopropyl ether, dichloromethane and acetonitrile.

* * * * *